United States Patent [19]

Steigerwald et al.

[11] Patent Number: 5,608,771
[45] Date of Patent: Mar. 4, 1997

[54] CONTACTLESS POWER TRANSFER SYSTEM FOR A ROTATIONAL LOAD

[75] Inventors: Robert L. Steigerwald, Burnt Hills; John A. Mallick, Scotia; John N. Park, Rexford, all of N.Y.

[73] Assignee: General Electric Company, Schenectady, N.Y.

[21] Appl. No.: 547,078

[22] Filed: Oct. 23, 1995

[51] Int. Cl.$^6$ ........................................ A61B 6/03
[52] U.S. Cl. ........................................... 378/15
[58] Field of Search ........................ 336/120; 378/15

[56] References Cited

U.S. PATENT DOCUMENTS

| | | | |
|---|---|---|---|
| 4,323,781 | 4/1982 | Baumann et al. | 378/15 |
| 4,912,735 | 3/1990 | Beer | 378/15 |
| 5,347,256 | 9/1994 | Yumiki et al. | 336/84 C |

FOREIGN PATENT DOCUMENTS

| 0154309 | 7/1991 | Japan | 336/120 |
|---|---|---|---|

*Primary Examiner*—David P. Porta
*Assistant Examiner*—David Vernon Bruce
*Attorney, Agent, or Firm*—Jill M. Breedlove; Marvin Snyder

[57] ABSTRACT

Power is transferred from a stationary power supply to a rotational gantry in a computer tomography (CT) system through a rotary transformer arranged in a ring configuration with an inner diameter that is sufficiently large to receive a patient. The rotary transformer has a toroidal rotor core and a toroidal stator core arranged either concentrically with an air gap extending radially therebetween or side-by-side with an air gap extending axially therebetween. A resonant inverter provides ac power to the rotary transformer which, in turn, drives a high-voltage tank circuit coupled to a x-ray tube, the tank circuit and x-ray tube being mounted on a rotational gantry. Advantageously, this is a contactless power transfer system which eliminates conventional brush and slip ring arrangements and moreover avoids the need for mounting the inverter to rotate with the CT gantry.

7 Claims, 4 Drawing Sheets

CONTACTLESS POWER TRANSFER SYSTEM FOR A ROTATIONAL LOAD

FIELD OF THE INVENTION

The present invention relates generally to a mechanism for transferring power from a stationary power supply to a rotational load and, more particularly, to such a mechanism which does not require contact (e.g., via a brush and slip ring arrangement) between the stationary power supply and the rotational load.

BACKGROUND OF THE INVENTION

In a conventional computer tomography (CT) system, power is transferred across a brush and slip ring mechanism to an inverter which rotates with the gantry and high-voltage tank circuit (i.e., transformer, rectifier, and filter capacitance) of the CT system. Unfortunately, placing the inverter on the rotational gantry increases the weight and complexity of the system. Furthermore, brush and slip ring mechanisms, which are required to carry appreciable current, are subject to reduced reliability, maintenance problems, and electrical noise generation which interferes with sensitive modern medical diagnostic procedures, especially in harsh environments.

Accordingly, it is desirable to provide a mechanism for transferring power from a stationary power supply to a rotational load (e.g., in a CT system) in a contactless manner, i.e., without the need for a brush and slip ring mechanism and without increasing the complexity of the circuitry involved in the power conversion. It is also desirable to remove the inverter from the rotational gantry of a CT system and place it on the stationary side where it may be easily and conveniently packaged. It is furthermore desirable to reduce the weight and complexity of the rotational gantry of a CT system while increasing the reliability of the power transfer mechanism.

SUMMARY OF THE INVENTION

Power is transferred from a stationary power supply to a rotational gantry in a computer tomography (CT) system through a rotary transformer arranged in a ring configuration with an inner diameter that is sufficiently large to receive a patient. The rotary transformer comprises a toroidal rotor core and a toroidal stator core arranged either concentrically with an air gap extending radially therebetween or side-by-side with an air gap extending axially therebetween. A resonant inverter provides ac power to the rotary transformer which, in turn, drives a high-voltage tank circuit coupled to an x-ray tube, the tank circuit and the x-ray tube being mounted on the rotational gantry. Advantageously, this is a contactless power transfer system which eliminates conventional brush and slip ring arrangements and moreover avoids the need for mounting the inverter to rotate with the CT gantry.

BRIEF DESCRIPTION OF THE DRAWINGS

The features and advantages of the present invention will become apparent from the following derailed description of the invention when read with the accompanying drawings in which.

DETAILED DESCRIPTION OF THE INVENTION

Figure 1:
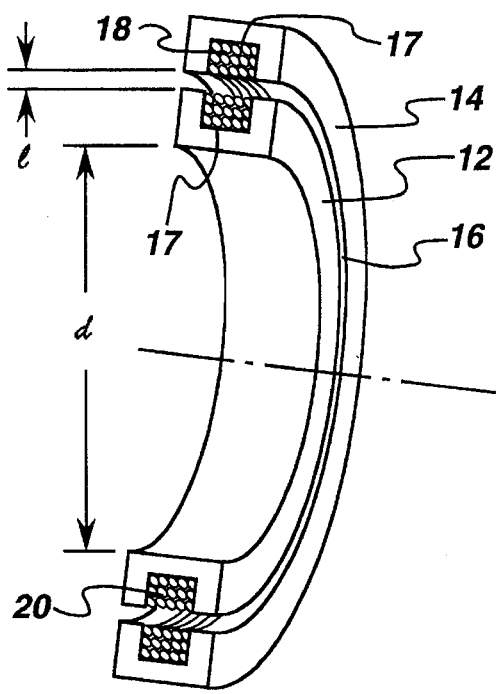
FIG. 1 is a cross sectional view of a rotary transformer useful in the contactless power transfer system of the present invention.

FIG. 1 is a cross sectional view of a toroidal rotary transformer 10 according to the present invention. The inner diameter d of an exemplary toroidal rotary transformer useful in a computer tomography (CT) system is sufficiently large (e.g., on the order of four feet) to allow for insertion of a patient therein. The transformer 10 of FIG. 1 has a rotor core 12 with a C-shaped cross section and a stator core 14 with a C-shaped cross section, each having a winding slot 17. There is a radial air gap 16 of length l between the rotor 12 and the stator 14. A primary winding 18 is wound circumferentially in a single direction on the stator 14, and a secondary winding 20 is wound circumferentially in a single direction on the rotor 12.

In general, it is desirable to minimize the length l of the air gap 16 in order to minimize the leakage inductance between the primary and secondary windings. The air gap 16 between the rotor 12 and the stator 14 may be on the order of 10 to 100 mils, for example.

Figure 2:
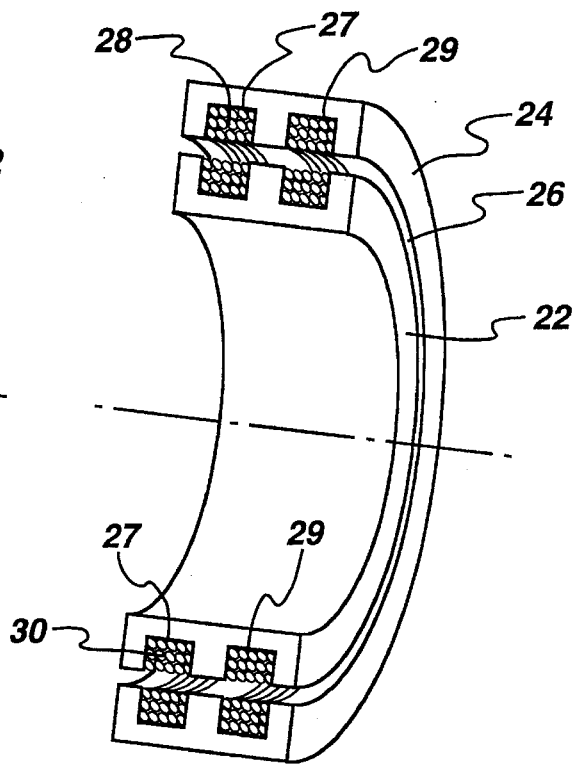
FIG. 2 is a cross sectional view of an alternative embodiment of a rotary transformer useful in the contactless power transfer system of the present invention.

FIG. 2 illustrates an alternative embodiment of a rotary transformer according to the present invention with a rotor 22 and a stator 24, each having a core with an E-shaped cross section with two winding slots 27 and 29, and a radial air gap 26 between the stator and the rotor. A primary winding 28 is wound in one direction in one slot 27 and returns in the opposite direction in the other slot 29; the secondary winding 30 is likewise wound in opposite directions in the two secondary slots.

Advantageously, for both the C-core and E-core configurations, the external magnetic fields are very small near a patient using the CT system due to the magnetic field cancellation between the primary and secondary windings. However, the magnetic field cancellation in the E-core configuration is more nearly complete than in the C-core configuration due to the return path for the primary and secondary windings. On the other hand, the C-core configuration is somewhat simpler and easier to construct.

Although the rotating member, i.e., rotor, for the radial configurations of FIGS. 1 and 2 are shown as being situated inside the stationary member, i.e., stator, an alternative embodiment has the outside member as the rotatable member with the inside member being stationary.

Figure 3:
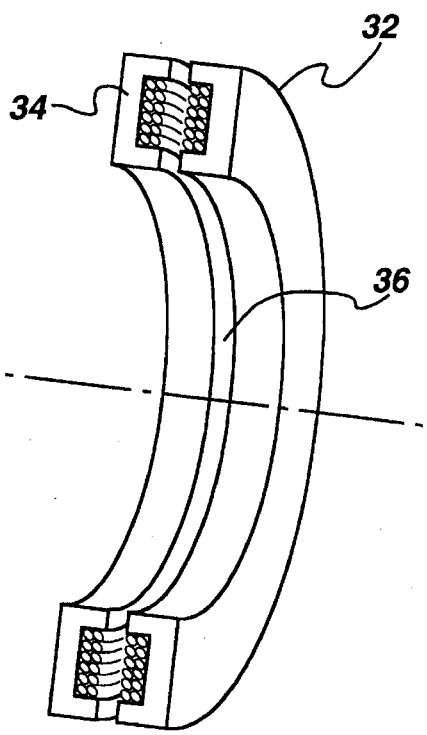
FIG. 3 is a cross sectional view of another alternative embodiment of a rotary transformer useful in the contactless power transfer system of the present invention.
Figure 4:
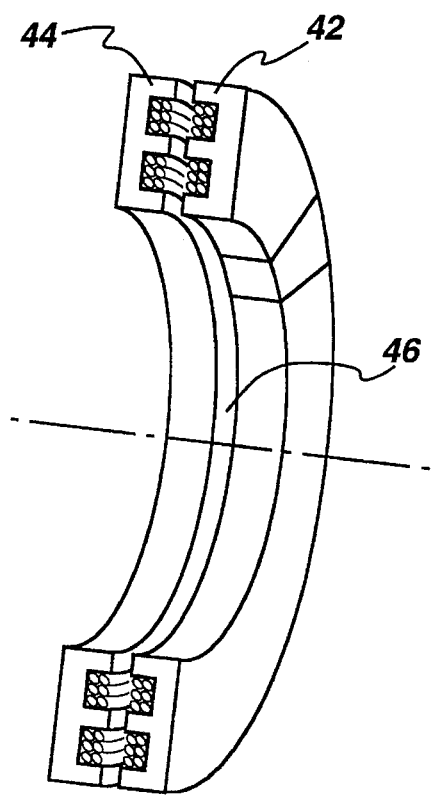
FIG. 4 is a cross sectional view of another alternative embodiment of a rotary transformer useful in the contactless power transfer system of the present invention.

FIGS. 3 and 4 illustrate alternative embodiments of rotary transformers according to the present invention, each with an axial air gap 36 and 46, respectively. FIG. 3 has a rotor core 32 with a C-shaped cross section and a stator core 34 with a C-shaped cross section; and FIG. 4 has a rotor 42 with an E-shaped cross section and a stator 44 with an E-shaped cross section. In the C-shaped configuration of FIG. 3, the primary and secondary windings extend in a single direction in the single winding slot. In the E-shaped configuration of FIG. 4, the primary and secondary windings each have a return path.

The cross sectional C-core and E-core configurations may be constructed by stacking commercially available C- or E-cores. Typical cores comprise ferromagnetic or ferrimagnetic materials.

Figure 5:
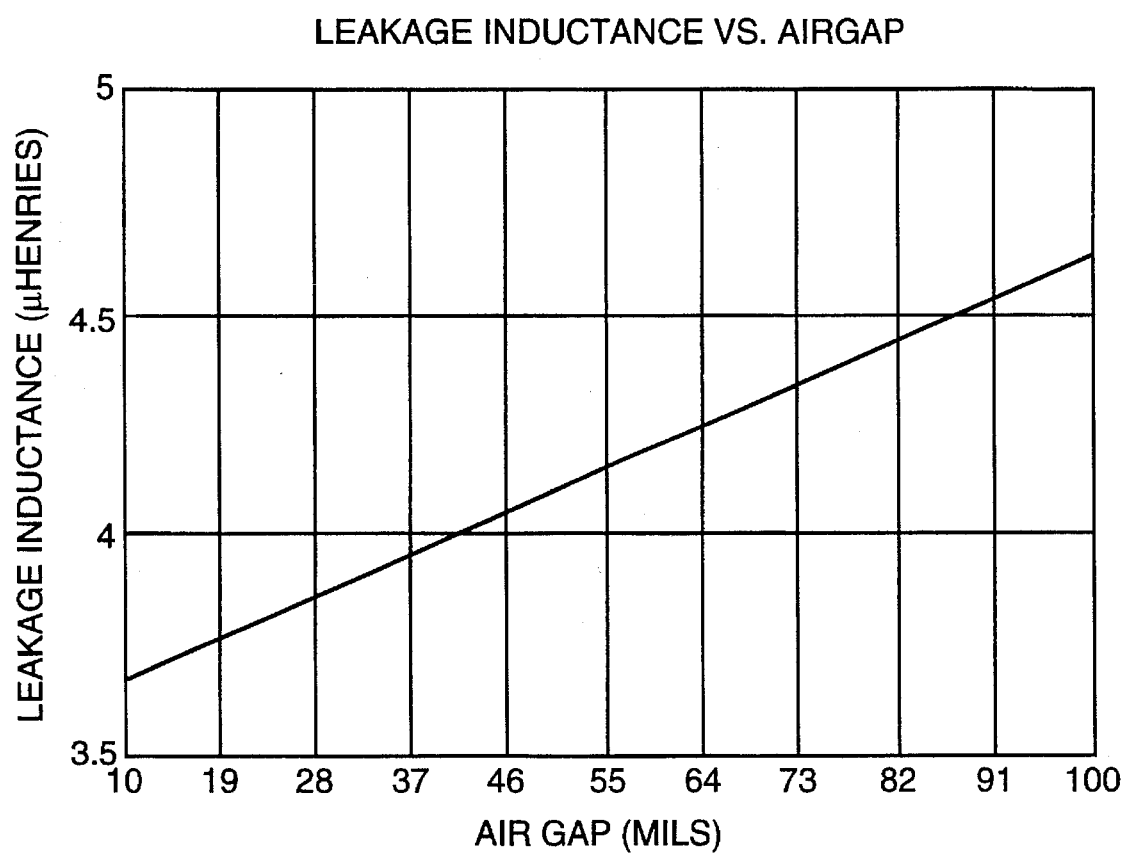
FIG. 5 graphically illustrates the calculated effect of air gap on leakage inductance for a rotary transformer according to the present invention.

FIG. 5 graphically illustrates the effect of air gap on leakage inductance for exemplary rotary transformers of the present invention. As illustrated, as the air gap widens, leakage inductance increases. The values given in FIG. 5 are in a range wherein they can serve as part of the resonant inductance of a resonant converter and actually reduce the size of the external resonant inductance Lr needed for the converter.

Figure 6:
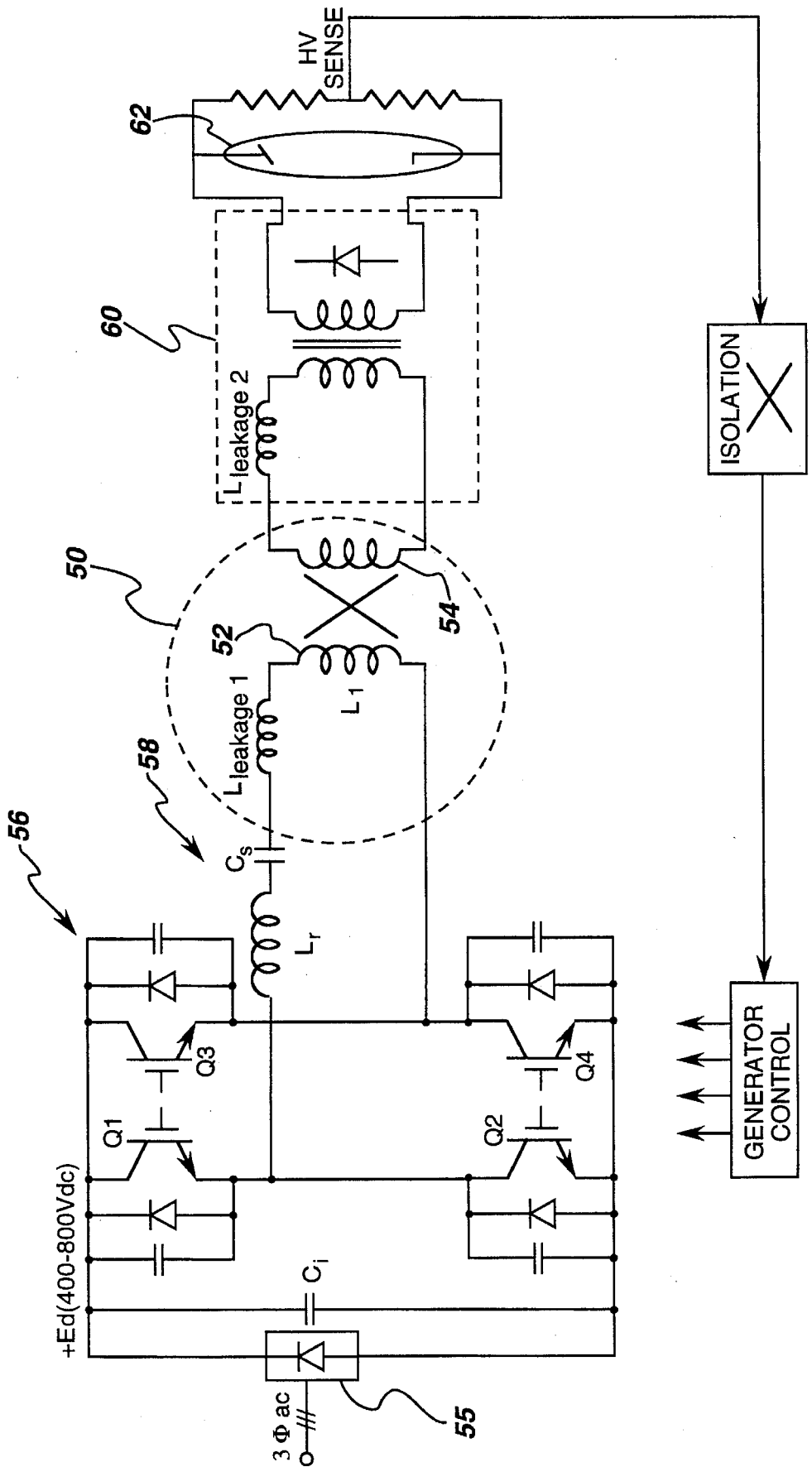
FIG. 6 schematically illustrates a contactless power transfer system in accordance with the present invention.

FIG. 6 schematically illustrates an exemplary CT system using a rotary transformer 50 according to the present invention with primary winding 52 and secondary winding 54 and leakage inductance Lleakage1, such as of a type illustrated in FIGS. 1–4. The CT system of FIG. 5 includes a rectifier 55 for receiving a three-phase input ac voltage. A filter capacitor Ci is connected across the rectifier 55. An inverter 56, shown by way of example as a full-bridge inverter with switching devices Q1–Q4, is connected across the input capacitor Ci. A resonant circuit 58, illustrated as a series resonant circuit Lr, Cs, situated on the stationary side, is used to tone out the leakage inductance Lleakage1 due to imperfect coupling of the rotary transformer in series with the leakage inductance Lleakage2 of a high-voltage tank circuit 60 mounted on a rotational gantry (see FIG. 7). In fact, the transformer leakage inductances Lleakage1 and Lleakage2 serve as pan of the resonant inductance Lr required by the circuit and actually reduces the size needed for external resonant inductance Lr. The high-voltage tank circuit 60 is coupled across an x-ray tube (i.e., CT scanner) 62. Advantageously, using the rotary transformer according to the present invention, the inverter 56 does not have to rotate with the gantry which is used to support the high-voltage tank and the x-ray tube as in conventional systems to reduce noise caused by ac power passing through slip rings, but may be packaged conveniently on the stationary side.

As an alternative embodiment to that of FIG. 6, the secondary winding 54 of the rotary transformer 50 may comprise the high-voltage secondary winding of the high-voltage tank circuit 60, thereby eliminating the transformer in the high-voltage tank circuit.

Figure 7:
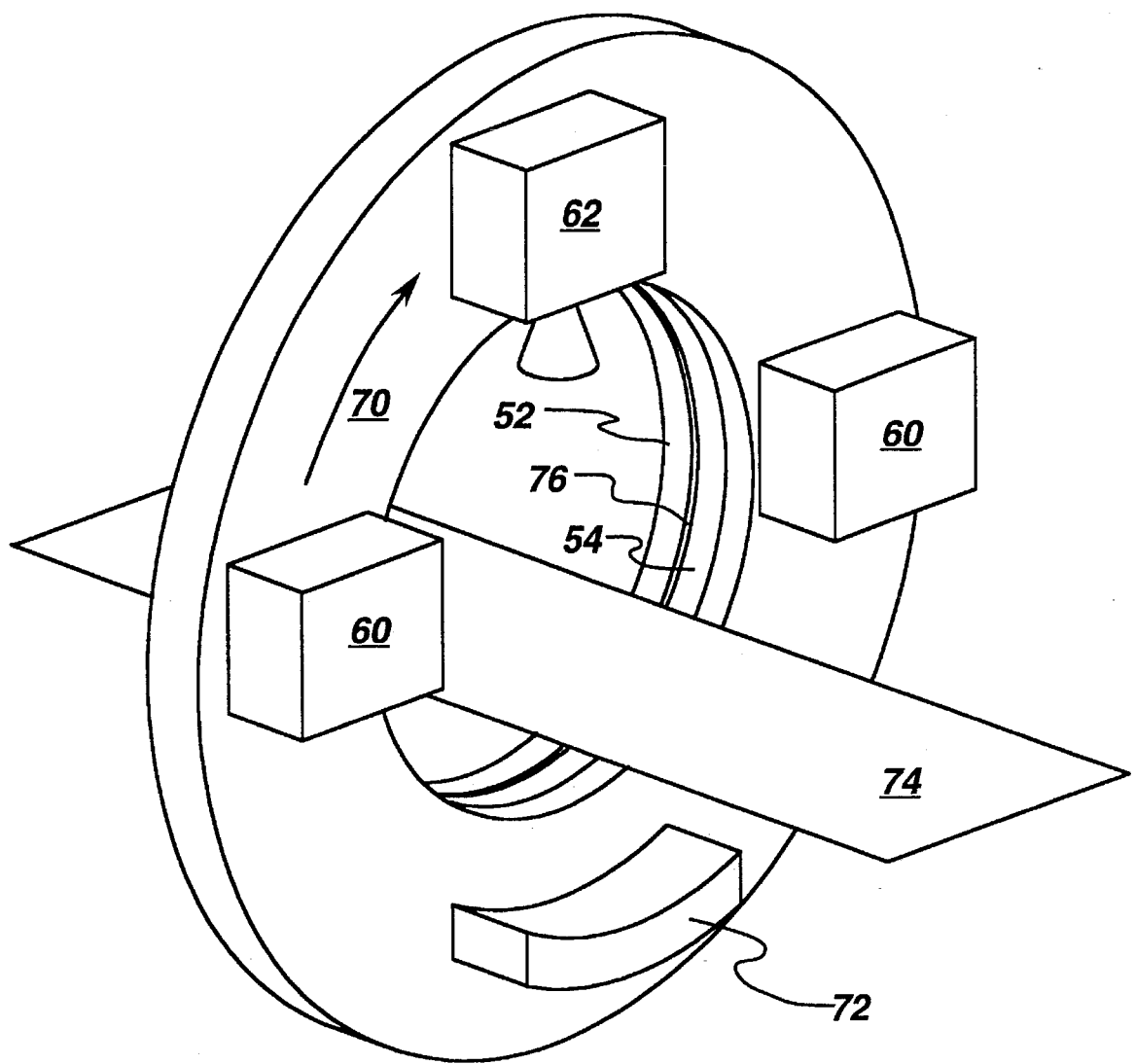
FIG. 7 is a perspective view illustrating a rotational gantry using a contactless power transfer system in accordance with the present invention.

FIG. 7 illustrates, in perspective view, an exemplary CT system such as that of FIG. 6 wherein a toroidal, rotational gantry 70 has x-ray tube 62 and a detector array 72 associated therewith and high-voltage tank circuits 60 (two of which are provided for electrical and mechanical balance) mounted thereon with a patient platform 74 situated in the center thereof. The rotational secondary winding 54 of the rotary transformer 50 is mounted on the rotational gantry 70, and the stationary primary winding 52 of the rotary transformer 50 is situated in close proximity to the secondary winding 52 with an air gap 76 therebetween. Although rotary transformer 50 is shown in FIG. 7 as comprising an axially extending air gap 76, it is to be understood that a rotary transformer comprising a radially extending air gap, such as described hereinabove, could alternatively be used.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A computer tomography system, comprising:
    a rotational gantry for mounting an x-ray tube and a detector array thereon;
    a resonant inverter for converting an input dc voltage to an ac voltage for driving said x-ray tube, said resonant inverter comprising a resonant output circuit;
    a high-voltage tank circuit coupled through a rotary transformer to said resonant inverter, said tank circuit also being mounted on said gantry;
    said rotary transformer comprising a rotor having a rotational toroidal-shaped core with at least one winding wound thereon and a stator having a stationary toroidal-shaped core with at least one winding wound thereon, said rotor core and stator core having an air gap therebetween, one of the windings of said rotary transformer being of sufficiently high voltage such that said high-voltage tank circuit does not require a separate respective transformer, said rotor core and said stator core being arranged in a ring configuration with an inner diameter sufficiently large to receive a patient.

2. The computer tomography system of claim 1 wherein said rotor core and stator core are situated concentrically with respect to each other, said air gap extending radially between said rotor core and said stator core.

3. The computer tomography system of claim 1 wherein said rotor is situated inside said stator.

4. The computer tomography system of claim 1 wherein said stator is situated inside said rotor.

5. The computer tomography system of claim 1 wherein said rotor core and said stator core have substantially the same dimensions and are situated side-by-side with said air gap extending axially therebetween.

6. The computer tomography system of claim 1 wherein said rotor core and said stator core each have a substantially C-shaped cross section.

7. The computer tomography system of claim 1 wherein said rotor core and said stator core each have a substantially E-shaped cross section.

* * * * *